(12) United States Patent
Honma

(10) Patent No.: US 6,225,336 B1
(45) Date of Patent: May 1, 2001

(54) COMPOUNDS HAVING [2.2.1] BICYCLO SKELETON

(75) Inventor: Tsunetoshi Honma, Nara (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/485,544

(22) PCT Filed: Sep. 7, 1998

(86) PCT No.: PCT/JP98/03991
§ 371 Date: Feb. 14, 2000
§ 102(e) Date: Feb. 14, 2000

(87) PCT Pub. No.: WO99/15502
PCT Pub. Date: Jan. 4, 1999

(30) Foreign Application Priority Data

Sep. 19, 1997 (JP) .................................... 9-254002

(51) Int. Cl.[7] ...................... C07D 333/68; C07D 333/38; C07D 333/54; A61K 31/38
(52) U.S. Cl. ........................... 514/443; 514/445; 514/448; 548/492; 549/51; 549/55; 549/57; 549/64; 549/72; 549/471
(58) Field of Search ................. 549/51, 55, 57, 549/64, 72; 514/443, 445, 448

(56) References Cited

U.S. PATENT DOCUMENTS

| | | |
|---|---|---|
| 4,792,550 | 12/1988 | Miyake et al. . |
| 4,861,913 | 8/1989 | Narissada et al. .................... 562/427 |

FOREIGN PATENT DOCUMENTS

| | | |
|---|---|---|
| 0 837 052 A1 | 4/1998 | (EP) . |
| 53295 | 9/1991 | (JP) . |
| WO 97/00853 | 9/1997 | (WO) . |

OTHER PUBLICATIONS

H. Gilman et al., "Dbenzothiophene: Orientation and Derivatives," pp. 108–119 (1938), J. Organic Chem.

B.P. Das et al., J. of Med. Chem., vol. 15, No. 4, "Naphthothiophenes. 1. α–(Alkylaminomethyl)–4–naphtho[2,1–b] thiophenemethanols as Antimalarials," pp. 370–375 (1972).

P.A. Plé et al., J. Heterocyclic Chem., vol. 25, "Synthesis of Substituted Benzo[b]thiophenes by Acid–Catalyzed Cyclization of Thiophenylacetals and Ketones," pp. 1271–1273 (1988).

S. Kano et al., Heterocycles, vol. 20, No. 10, "Synthesis of 2–Substituted 3,5–Dibromothiophenes through Base–Catalyzed Halogen Dance Reaction of 2,5–Dibromothiophene," pp. 2035–2037 (1983).

G.C. Crawley et al., J. Med. Chem., vol. 38, "Chiral Dioxolane Inhibitors of Leukotriene Biosynthesis: Structure–Activity Relationships and Syntheses Uisng Asymmetric Dihydroxylation," pp. 3951–3956 (1995).

G.M. Badger et al., "Thionaphthencarboxylic Acids," pp. 2624–2631 (1957), J. Chem. Soc.

A. Arimura et al., Int. Arch. Allergy Immunol, vol. 98, "Antiasthmatic Activity of a Novel Thromboxane $A_2$ Antagonist, S–1452, in Guinea Pigs," pp. 239–246 (1992).

T. Tsuri et al., J. Med. Chem., vol. 40, No. 22, "Bicyclo [2.2.1]heptane and 6,6–Dimethylbicyclo[3.1.1]heptane Derivatives: Orally Active, Potent, and Selective Prostaglandin $D_2$ Receptor Antagonists," pp. 3504–3507 (1997).

*Primary Examiner*—Bernard Dentz
(74) *Attorney, Agent, or Firm*—Foley & Lardner

(57) ABSTRACT

This invention provides novel compounds which are dual antagonistic to $TXA_2$ and $PGD_2$ receptors and the pharmaceutical compositions containing them. They are useful for treating, for example, systemic mastocytosis and disorder of systemic mast cell activation as well as tracheal contraction, asthma, allergic rhinitis, allergic conjunctivitis, urticaria, ischemic reperfusion injury, and inflammation.

In detail, this invention provides a compound of the foumula (I):

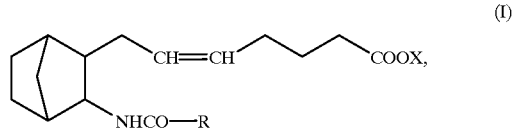

pharmaceutically acceptable salt thereof, or hydrate thereof.

10 Claims, No Drawings

COMPOUNDS HAVING [2.2.1] BICYCLO SKELETON

This application is a 371 of PCT/JP98/03991 filed Sep. 3, 2000.

TECHNICAL FIELD

This invention relates to compounds having a [2.2.1] bicyclo skeleton, and pharmaceutical compositions containing them antagonistic to both of thromboxane $A_2$ and prostagrandin $D_2$.

BACKGROUND ART

Some compounds having a [2.2.1] bicyclo skeleton similar to the compounds of the present invention have been described in the Japanese Patent Publication (Kokoku) No. 53295/1991. In this publication, it is described that the compounds are useful as thromboxane $A_2$ ($TXA_2$) antagonists. $TXA_2$ has been known to have various activities such as platelet aggregation, thrombogenesis, etc. The $TXA_2$ antagonists which antagonize $TXA_2$ have, therefore, been considered to be useful as anti-thrombotic agents as well as medicines for treating myocardinal infarction or asthma.

Further, the other compounds having a [2.2.] bicyclo skeleton similar to the compounds of the present invention have been described in WO97/00853. In this publication, it is described that the compounds are useful as prostagrandin $D_2$ ($PGD_2$) antagonists. $PGD_2$ is a major prostanoid released from mast cells in which it is produced through $PGG_2$ and $PGH_2$ from arachidonic acid by the action of cyclooxygenase activated by immunological or unimmunological stimulation. $PGD_2$ has various potent physiological and pathological activities. For example, $PGD_2$ can cause strong contraction of smooth muscle of bronchus to lead to bronchial asthma, and in a systemic allergic state, it dilates the peripheral vessels to cause an anaphylactic shook. Accordingly, $PGD_2$ antagonists are useful for the improvement of conditions caused by excessive production of $PGD_2$, particularly as drugs for treating diseases involved with mast cell dysfunction, for example, systemic mastocytosis and disorder of systemic mast cell activation as well as tracheal contraction. asthma, allergic rhinitis, allergic conjunctivitis, urticaria, atopic dermatitis, alimentary allergy, cerebrovascular disorder, ischemic reperfusion injury, and inflammation.

As shown above, $PGD_2$ antagonists have quite a different character from that of $TXA_2$ antagonists in the site of action, mechanism of action, and indication thereof.

On the other hand, $TXA_2$ and $PGD_2$ dual antagonistic compounds could be useful as therapeutic agents treating various diseases caused by $TXA_2$ or PGD2. For example, it is known that $TXA_2$ has a strong activity for tracheal contraction and respiratory anaphilaxia, and recently known that $PGD_2$ has an activity for infiltration of eosionophils. From these comprehension, $TXA_2$ and $PGD_2$ are thought to be one of causative substances of the pathopoiesis and advance of asthma, thus the dual antagonistic compounds are expected to be possible more useful agents for treating asthma than each of the known antagonists. Further, in case of allergic rhinitis, it is recognized that $TXA_2$ and $PGD_2$ cause the swelling of nasal mucosa through the aggravation of vascular permeability, and $PGD_2$ induces the nasal blockage through the enlargement of vascular volume. It is therefore expected to develop drugs having a dual antagonistic activity.

As shown above, the compounds having a dual antagonistic activity are expected to be used for many indications and to exhibit new excellent therapeutic effects which have not yet been.

DISCLOSURE OF INVENTION

The present inventors have studied intensively to develop $PGD_2$ receptor antagonists (blockers) specific to the $PGD_2$ receptor, and found out a new series of compounds which are useful not only as $PGD_2$ receptor antagonists but also as $TXA_2$ receptor antagonists and are of high safety, whereby accomplished the present invention.

Accordingly, the present invention provides a compound of the formula (I):

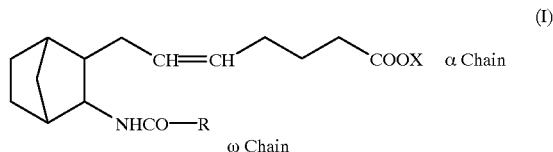

wherein R is an optionally substituted monocyclic or condensed heterocycle, provided that R is not an optionally substituted dibenzofuryl, X is hydrogen or an alkyl, and the double bond has E configuration or Z configuration, pharmaceutically acceptable salt thereof, or hydrate thereof, and a $TXA_2$ and $PGD_2$ antagonistic pharmaceutical composition comprising them, preferably a pharmaceutical composition for treating asthma or nasal blockage comprising them.

Best Mode for Carrying Out the Invention

In the above formula, "optionally substituted monocyclic or condensed heterocycle" for R means a 5–7 membered ring containing one or more hetero atoms selected from the group consisting of oxygen, sulfur, and nitrogen atoms in the ring, or such a heterocycle as condensed with one or more carbocycle or other heterocycle and both rings may have a bond and substituent(s) at any substitutable position(s), provided that R does not include an optionally substituted dibenzofuryl.

The term "carbocycle or other heterocycle" means a 5–7 membered ring which may have one or more hetero atoms selected from the group consisting of oxygen, sulfur, and nitrogen atoms in the ring, or a condensed ring consisting of two or more of such rings.

Examples of "monocyclic or condensed heterocycle" include pyrrolidinyl (e.g., 2-pyrrolidinyl), pyrrolyl (e.g., 2-pyrrolyl, 3-pyrrolyl), piperidinyl (e.g., 3-piperidinyl, 4-piperidinyl), pyridyl (e.g., 3-pyridyl, 4-pyridyl), pyrazolyl (e.g., 3-pyrazolyl), imidazolyl (e.g., 2-imidazolyl, 3-imidazolyl), piperazinyl (e.g., 2-piperazinyl), pyrimidinyl (e.g., 4-pyrimidinyl), pyrazinyl (e.g., 2-pyrazinyl), indolyl (e.g., 2-indolyl, 3-indolyl), carbazolyl (e.g., 3-carbazolyl), benzoimidazolyl (e.g., 2-benzoimidazolyl), indazolyl (e.g., 3-indazolyl), quinolyl (e.g., 8-quinolyl), isoquinolyl (e.g., 3-isoquinolyl), tetrahydrofuryl (e.g., 3-tetrahydrofuryl), furyl (e.g., 2-furyl, 3-furyl), benzofuryl (e.g., 2-benzofuryl, 3-benzofuryl), tetrahydrothienyl (e.g., 2-tetrahydrothienyl, 3-tetrahydrothienyl), thienyl (e.g., 2-thienyl, 3-thienyl), benzothienyl (e.g., benzo[b]thiophen-2-yl, benzo[b]thiophen-3-yl), dibenzothienyl (e.g., 2-dibenzothienyl, 3-dibenzothienyl), tetrahydrodibenzothienyl (e.g., 1,2,3,4-tetrahydrodibenzothienyl), naphthothienyl (e.g., naphtho[2,3-b]thienyl, naphtho[1,2-b]thienyl), oxazolyl (e.g., 2-oxazolyl), isoxazolyl (e.g., 4-isoxazolyl), thiazolyl e.g., 2-thiazolyl, 4-thiazolyl), isothiazolyl (e.g., 3-isothiazolyl, 4-isothiazolyl), and the like.

The preferable embodiment of "monocyclic or condensed heterocycle" is an aromatic monocyclic or condensed heterocycle such as pyrrolyl (e.g., 2-pyrrolyl, 3-pyrrolyl), pyridyl (e.g., 3-pyridyl, 4-pyridyl), pyrazolyl (e.g., 3-pyrazolyl), imidazolyl (e.g., 2-imidazolyl, 3-imidazolyl), pyrimidinyl (e.g., 4-pyrimidinyl), pyrazinyl (e.g., 2-pyrazinyl), indolyl (e.g., 2-indolyl, 3-indolyl), carbazolyl (e.g., 3-carbazolyl), benzoimidazolyl (e.g., 2-benzoimidazolyl), indazolyl (e.g., 3-indazolyl), quinolyl (e.g., 8-quinolyl), isoquinolyl (e.g., 3-isoquinolyl), furyl (e.g., 2-furyl, 3-furyl), benzofuryl (e.g., 2-benzofuryl, 3-benzofuryl), thienyl (e.g., 2-thienyl, 3-thienyl), benzothienyl (e.g., benzo [b]thiophen-2-yl, benzo[b]thiophen-3-yl), dibenzothienyl (e.g., 2-dibenzothienyl, 3-dibenzothienyl), tetrabydrodibenzothienyl (e.g., 1,2,3,4-tetrahydrodibenzothienyl), naphthothienyl (e.g., naphtho[2,3-b]thienyl, naphtho[1,2-b]thienyl), oxazolyl (e.g., 2-oxazolyl), isoxazolyl (e.g., 4-isoxazolyl), thiazolyl (e.g., 2-thiazolyl, 4-thiazolyl), isothiazolyl (e.g., 3-isothiazolyl, 4-isothiazolyl), and the like.

The present invention includes a compound of the formula (I) wherein R is an optionally substituted monocyclic or condensed heterocycle containing only a sulfur atom(s) as hetero atom.

"Optionally substituted monocyclic or condensed heterocycle containing only a sulfur atom(s) as hetero atom" includes the following groups which are optionally substituted:

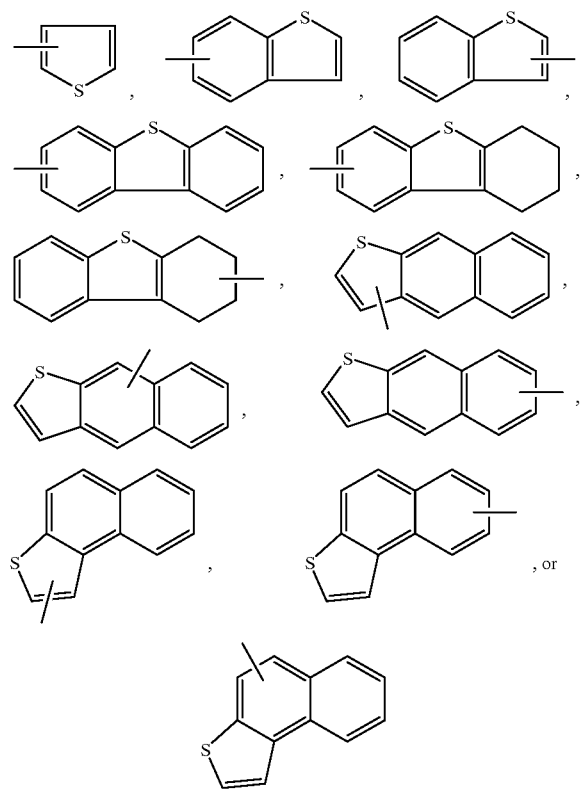

The substituents of "optionally substituted monocyclic or condensed heterocycle" include a substituent selected from an alkyl an alkenyl, an acyl, an alkoxy, an alkylthio, an acyloxy, hydroxy, a halogen, nitro, and a substituted or unsubstituted amino. The substituent may bind to one to three of any substitutable positions on the ring.

Throughout the specification, the term "alkyl", used itself or combined with other terms, means a C1–C8 straight or branched chain alkyl or a C3–C8 cycloalkyl, for example, methyl, ethyl, n-propyl, i-propyl, n-butyl, i-butyl, tert-butyl, n-pentyl, i-pentyl, n-hexyl, n-heptyl, n-octyl, cyclopropyl, cyclobutyl, cyclopentyl, cyclohexyl, cycloheptyl, and the like.

Throughout the specification, the term "alkenyl", used itself or combined with other terms, means a C2–C8 straight or branched chain alkenyl or a C3–C8 cycloalkenyl, which has one or more double bonds, for example, vinyl, 1-propenyl, 2-propenyl, i-propenyl, 2-cyclobuten-1-yl, 2-cyclopenten-1-yl, 3-cyclopenten-1-yl, 2-cyclohexen-1-yl, and the like.

Throughout the specification the term "acyl", used itself or combined with other terms, means an alkylcarbonyl or an alkenylcarbonyl, for example, acetyl, propionyl, butyryl, isobutyryl, valeryl, isovaleryl, pivaloyl, acryloyl, metaacryloyl, and the like.

Throughout the specification, the term "alkoxy", used itself or combined with other terms, means an alkyloxy, for example, methoxy, ethoxy, n-propoxy, i-propoxy, n-butoxy, and the like.

Examples of "alkylthio" include methylthio, ethylthio, propylthio, and the like.

Examples of "acyloxy" include acetyloxy, propionyloxy, butyryloxy, isobutyryloxy, valeryloxy, isovaleryloxy, pivaloyloxy, metaacryloyloxy, and the like.

The term "halogen" means fluorine, chlorine, bromine, and iodine.

The term "substituted or unsubstituted amino" means an optionally substituted amino, and the substitutions include, for example, alkyl, alkenyl, acyl, alkoxycarbonyl, or alkylsulfonyl, and the like. Examples of the alkoxycarbonyl include methoxycarbonyl, ethoxycarbonyl, n-propoxycarbonyl, i-propoxycarbonyl, n-butoxycarbonyl, t-butoxycarbonyl, and the like. Examples of the alkylsulfonyl include methylsulfonyl, ethylsulfonyl, n-propylsulfonyl, i-propylsulfonyl, n-butylsulfonyl, t-butylsulfonyl, and the like.

The preferable embodiment of "optionally substituted monocyclic or condensed heterocycle" is a monocyclic or condensed aromatic heterocycle, which is unsubstituted at all or substituted with hydroxy or halogen, and contains sulfur atom only as a hetero atom.

In the above formula (1), preferable R is a group represented by the following formula:

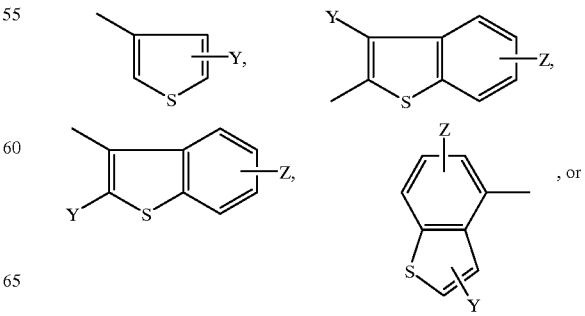

-continued

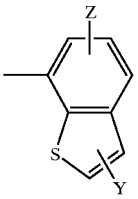

wherein Y and Z each is independently hydrogen, hydroxy, or a halogen.

More preferable R is represented by the formula:

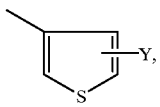 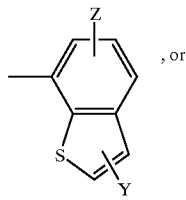, or

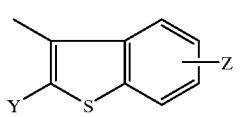

wherein Y and Z are as defined above.

The compounds of the present invention can be any of the following stereo isomers of [2.9.1] bicyclo skeleton, thus the present invention includes all of them and the optional mixtures thereof. Namely, the bond binding to the bicyclic ring is in R configuration or S configuration, and all of the stereo isomers (diastereomer, epimer, enantiomer, and the like), racemates, and optional mixture thereof are included in the present invention,:

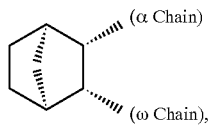 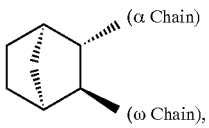

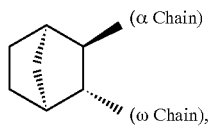 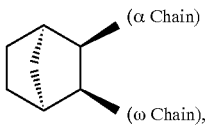

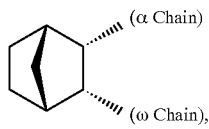 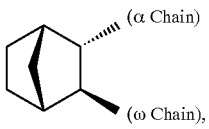

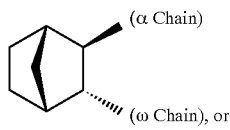 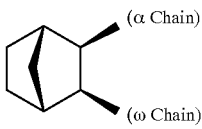

In these stereo isomers, the most preferable is a compound having the skeleton of the formula:

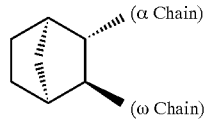

Moreover, the α chain of the compound of the present invention can be in Z configuration or E configuration, thus a compound having any of the configurations and the mixture thereof are included in the present invention.

As understood from the above explanations, a preferable embodiment is a compound of the formula (I'):

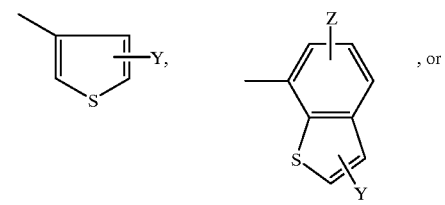 (I')

wherein R is a group of the formula:

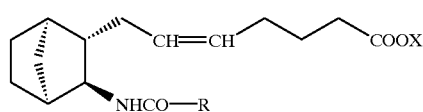, or

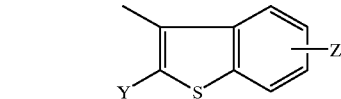

wherein Y and Z each is independently hydrogen, hydroxy, or a halogen, and the double bond has E configuration or Z configuration, pharmaceutically acceptable salt thereof, hydrate thereof.

More preferable compounds are shown below.

(A1) (5Z)-7-{(1R, 2S, 3S, 4S)-3-(5-Hydroxybenzo[b]thiophen-3-carbonylamino)-bicyclo[2.2.1]hept-2-yl}-5-heptenoic acid, (A2) ((5Z)-7-{(1R, 2S, 3S, 4S)-3-(Thiophen-3-carbonylamino)-bicyclo[2.2.1]hept-2-yl}-5-heptenoic acid, (A3) (5Z)-7-{(1R, 2S, 3S, 4S)-3-(Benzo[b]thiophen-7-carbonylamino)-bicyclo[2.2.1]hept-2-yl}-5-heptenoic acid, (A4) (5Z)-7-{(1R, 2S, 3S, 4S)-3-(Benzo[b]thiophen-3-carbonylamino)-bicyclo[2.2. 1]hept-2-yl}-5-heptenoic acid, (A5) (5Z)-7-{(1R, 2S, 3S, 4S)-3-(5-Fluorobenzo[b]thiophen-3-carbonylamino)-bicyclo[2.2.1]hept-2-yl}-5-heptenoic acid, (A6) (5Z)-7-{(1R, 2S, 3S, 4S)-3-(6-Hydroxybenzo[b]thiophen-2-carbonylamino)-bicyclo[2.2.1.]hept-2-yl}-5-heptenoic acid or (A7) (5Z)-7-{(1R, 2S, 3S, 4S)-3-(7-Hydroxybenzo[b]thiophen-2-carbonylamino)-bicyclo[2.2.1.]hept-2-yl}-5-heptenoic acid.

Examples of salts of the compounds (I) include those formed with an alkali metal (e.g. lithium, sodium, or potassium), an alkali earth metal (e.g. calcium), an organic base (e.g. tromethamine, trimethylamine, triethylamine, 2-aminobutane, t-butylamine, diisopropylethylamine, n-butylmethylamine, cyclohexylamine. dicyclohexylamine, N-isopropylcyclohexylamine, furfurylamine, benzylamine, methylbenzylamine, dibenzylamine, N,N-dimethylbenzylamine, 2-chlorobenzylamine, 4-metboxybenzylamine, 1-naphthalenemethylamine, diphenylbenzylamine, triphenylamine, 1-naphthylamine, 1-aminoanthracene, 2-aminoanthracene, dehydroabiethylamine, N-methylmorpholine, or pyridine), an amino acid (e.g. lysine, or arginine), and the like.

"Hydrate" means a hydrate of the compound of the formula (I) or of the salt, for example, monohydrate, dihydrate, and the like.

General processes for the preparation of the compounds of the present invention are illustrated as follows.

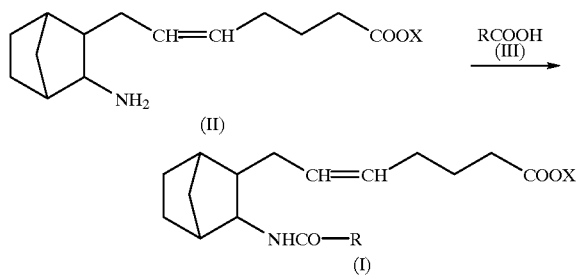

wherein R is an optionally substituted monocyclic or condensed heterocycle, provided that R is not an optionally substituted dibenzofuryl, X is hydrogen or an alkyl, and the double bond has E configuration or Z configuration.

As shown in the above process, the compound of the formula (1) can be prepared by reacting a carboxylic acid of the formula (III) or the reactive derivative with an amino compound of the formula (II).

In this process, the starting compound (II) wherein X is a methyl, 7-(3-amino-bicyclo[2.2.1]hept-2-yl)-5-heptenoic acid methyl ester is described in the Japanese Patent Publication (KoKoku) No. 79060/1993. The other starting compounds can be prepared in accordance with methods as described in the above publication.

The carboxylic acid of the formula (III) includes thiophene-3-carboxylic acid. benzo[b]thiophene-7-carboxylic acid, benzo[b]thiophene-3-carboxylic acid, 5-fluorobenzo[b]thiophene-3-carboxylic acid, 5-hydroxybenzo[b]thiophene-3-carboxylic acid, 6-hydroxybenzo[b]thiophene-3-carboxylic acid, and the like.

These carboxylic acids can be prepared in accordance with methods as described in J. Org. Chem., 3 108–119 (1938), J. Med. Chem., Vol. 15, No. 4, 370–373 (1972), J. Heterocyclic Chem., 25, 1271–1272 (1988), HETEROCYCLES. Vol. 20, No. 10, 2035–2037 (1983), J. Med. Chem. 38, 3951–3956 (1995), or J. Chem. Soc., 2624–2630 (1957).

The reactive derivatives of carboxylic acid of the formula (III) mean the corresponding acid halides (e.g., chloride, bromide, iodide), acid anhydrides (e.g., mixed acid anhydride with formic acid or acetic acid), active esters (e.g., succinimide ester), and the like, and include acylating agents used for the usual acylation of amino group. For example, an acid halide is obtained by reacting the compound (III) with a thionyl halide (e.g., thionyl chloride), phosphorous halide (e.g., phosphorous trichloride, phosphorous pentachloride), oxalyl halide (e.g., oxalyl chloride), and the like, in accordance with known methods as described in the literatures (e.g., Shin-Jikken-Kagaku-Koza, Vol. 14, 1787 (1978); Synthesis 852–854 (1986); Shin-Jikken-Kagaku-Koza Vol. 22, 115 (1992)).

The reaction can be conducted under a condition generally used for the acylation of amino group. For example, in the case of condensation with the acid halide, the reaction is carried out in a solvent such as an ether solvent (e.g., diethyl ether, tetrahydrofuran, dioxane), benzene solvent (e.g., benzene, toluene, xylene), halogenated hydrocarbon solvent (e.g., dichloromethane, dichloroethane, chloroform) as well as ethyl acetate, dimethylformamide, dimethyl sulfoxide, acetonitrile, or the like, if necessary, in the presence of a base (e.g., organic base such as triethylamine, pyridine, N,N-dimethylaminopyridine, N-methylmorpholine; inorganic base such as sodium hydroxide, potassium hydroxide, potassium carbonate, or the like) under cooling, at room temperature, or under heating, preferably at a temperature ranging from −20° C. to ice-cooling temperature, or from a room temperature to a refluxing temperature of the reaction system, for a period of several min to several hr, preferably for 0.5 hr to 24 hr, particularly, for 1 hr to 12 hr. In the case of using the carboxylic acid in a free form without converting into the reactive derivatives, the reaction is conducted in the presence of a condensing agent (e.g., dicyclohexylcarbodiimide (DCC), 1-ethyl-3-(3-methylaminopropyl) carbodiimide, N,N'-carbonyldiimidazole) usually used in the condensation reaction of amine and carboxylic acid.

For example, in the case of the compound (III) wherein R is substituted with hydroxy or amino, the compound can be reacted after protecting with acetyl group and the like in accordance with usual methods.

In the reaction of the other reactive derivatives or free acid with the amine (II), the reaction conditions are determined according to the property of each reactive derivative or free acid, in accordance with a known method. The reaction product can be purified in accordance with a conventional purification, such as the extraction with a solvent, chromatography, recrystallization, and the like.

In case of the introduction of a substituent(s) into the "optionally substituted monocyclic or condensed heterocycle", the change of the functional group can be performed before or after reacting a carboxylic acid or the reactive derivative thereof (III) with the amine (II). For example, in the case of the compound having a monocyclic or condensed aromatic heterocycle, the compound having an aromatic heterocycle substituted with nitro group can be obtained by the nitration with nitrating acid. Moreover, the compound having an aromatic heterocycle substituted with amino group can be obtained by the reduction of the above compound with tin in the presence of hydrochloride. Moreover, the compound having an aromatic heterocycle substituted with hydroxy group can be obtained by the diazonization of the above compound and hydrolysis with alkali. On the other hand, the compound having an aromatic heterocycle substituted with alkoxy group can be obtained by the reaction of diazonium derivative with alcohol. The compound having an aromatic heterocycle substituted with halogen can be obtained by Sandmeyer reaction, the reaction of the diazonium derivative with primary copper (e.g., $CuCl_2$, $CuBr_2$). The compound having an aromatic heterocycle substituted with halogen can be also obtained by the direct reaction of the compound having an aromatic heterocycle with chlorine and the like. Using the above-mentioned methods appropriately, halogen can be introduced into a desired position(s). The group of alkyl, alkenyl, or acyl group can be directly introduced into an aromatic heterocycle by Friedel Crafts reaction with alkyl agent, an alkenyl agent, or an acyl agent, respectively, in the presence of anhydrous aluminum chloride.

The objective compound (I) of the present invention can be converted into a corresponding ester derivative, if desired. For example, the ester derivative can be prepared by esterification of a carboxylic acid in accordance with a known method.

When using the compound (I) of the present invention in treatment, it can be formulated into ordinary formulations for oral and parenteral administration. A pharmaceutical composition containing the compound (I) of the present invention can be in the form for oral and parenteral administration. Specifically, it can be formulated into formulations for oral administration such as tablets, capsules, granules, powders, syrup, and the like; or those for parenteral administration such as injectable solution or suspension for intravenous, intramuscular, or subcutaneous injection, inhalant, eye drops, nasal drops, suppositories, or percutaneous formulations such as ointment.

In preparing the formulations, carriers, excipients, solvents, and bases known to one having ordinary skill in the art may be used. In case of tablets, they are prepared by compressing or fomulating an active ingredient together with auxiliary components. Examples of usable auxiliary components include pharmaceutically acceptable excipients such as binders (e.g., cornstarch), fillers (e.g., lactose, microcrystalline cellulose), disintegrants (e.g., starch sodium glycolate) or lubricants (e.g., magnesium stearate). Tablets may be coated appropriately. In case of liquid formulations such as syrups, solutions, or suspensions, they may contain suspending agents (e.g., methyl cellulose), emulsifiers (e.g., lecithin), preservatives, and the like. In case of injectable formulations, it may be in the form of solution, suspension, or oily or aqueous emulsion, which may contain suspension-stabilizing agents or dispersing agent, and the like. In case of an inhalant, it is formulated into a liquid formulation applicable to an inhaler. In case of eye drops, it is formulated into a solution or a suspension. Especially, in case of a nasal drug for treating nasal blockage, it can be used as a solution or suspension prepared by a conventional formulating method, or administered as a powder formulated using a powdering agent (e.g., hydroxypropyl cellulose, carbopole) into the nasal cavity. Alternatively, it can be used as an aerosol filled into a special container together with a solvent of low boiling point.

Although an appropriate dosage of the compound (I) varies depending on the administration route, age, body weight, sex, or conditions of the patient, and the kind of drug(s) used together, if any, and should be determined by the physician in the end, in the case of oral administration, the daily dosage can generally be between 0.01–100 mg, preferably 0.01–10 mg, more preferably 0.01–1 mg, per kg body weight. In case of parenteral administration, the daily dosage can generally be between 0.001–100 mg, preferably 0.001–1 mg, more preferably 0.001–0.1 mg, per kg body weight. The daily dosage can be administered in 1–4 divisions.

The following examples are provided to further illustrate the present invention and are not to be construed as limiting the scope.

EXAMPLE 1

Preparation of (5Z)-7-{(1R, 2S, 3S, 4S)-3-(5-Hydroxybenzo[b]thiophen-3-carbonylamino)-bicyclo[2.2.1]hept-2-yl)-5-heptanoic acid (1)

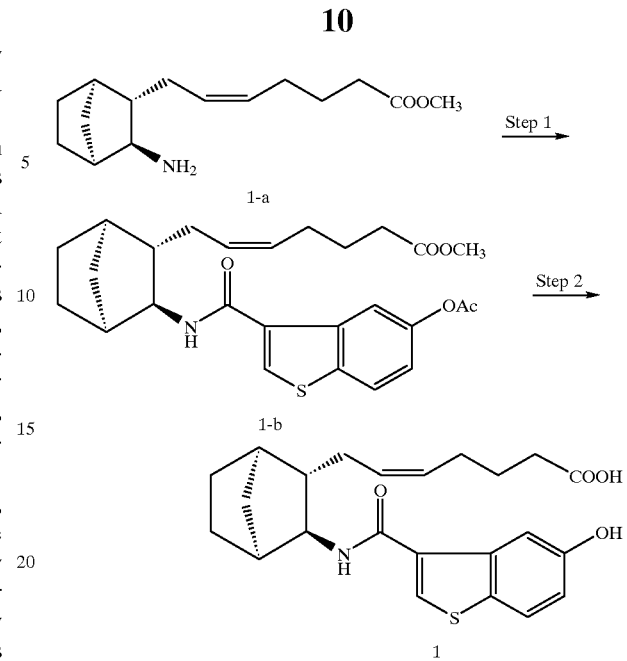

(Step 1)

To a solution of 251 mg (1.0 mmol) of amino compound (1-a) (described in Japanese Patent Publication (Kokoku No.79060/1993) in 5 ml of tetrahydrofuran were added 0.5 ml (3.6 mmol) of triethylamine and 255 mg (1.0 mmol) of 5-acetoxybenzo[b]thiophen-3-carbonyl chloride. After stirring for 1hour, the mixture was diluted with water, and extracted with toluene. The organic layer was washed with dilute hydrochloric acid and water, dried over anhydrous magnesium sulfate, and concentrated under reduced pressure. The residue was chromatographed on silica gel (toluene: ethyl acetate=9:1) to give 420 mg of the compound (1-b). Yield 89.4%.

The obtained compound was recrystallized from ethyl acetate and n-hexane (1: 3) to give 304 mg of needle crystals. Yield 64.7%. M.p. 87–88° C. $[\alpha]D^{26}+51.8°$ (c=1.01%, $CH_3OH$)

Elementary Analysis (for $C_{26}H_{31}NO_5S$) Calcd.(%): C, 66.50; H, 6.65; N, 2.98; S, 6.83 Found(%): C, 66.46; H, 6.67; N, 3.01; S, 6.95

(Step 2)

To a solution of 332 mg (0.71 mmol) of the above obtained compound (1-b) in 3 ml of methanol was added 0.61 ml (2.5 mmol) of 4N sodium hydroxide. After stirring for 2 hours at 42° C., the reaction mixture was neutralized with 2.5 ml of 1N hydrochloric acid, diluted with water, and extracted with ethyl acetate. The organic layer was washed with water, dried over anhydrous magnesium sulfate, and concentrated under reduced pressure. The residue was recrystallized from ethyl acetate/n-hexane (1:3) to give 250 mg of the compound (1) as needles. Yield (%) 85.6%. Mp 140–141.5° C. $[\alpha]D^{25}+57.3°$ (c=1.00%, $CH_3OH$)

Elementary Analysis (for $C_{23}H_{27}NO_4S$) Calcd.(%): C, 66.80; H, 6.58; N, 3.39; S, 7.75 Found(%): C, 66.57; H, 6.56; N, 3.28; S, 7.59

$^1$H NMR δ ($CDCl_3$), 300 MHz; 1.09 (1H, m), 1.20–1.34 (2H, m), 1.45–1.54 (2H, m), 1. 57–1.70 (4H, m), 1.96–2.32 (7H, m), 2.61 (1H, s), 3.90 (1H, m), 5.26–5.46 (2H, m), 6. 25 (1H, d, J=7.2 Hz), 7.01 (1H, dd, J=2.4 and 8.7 Hz), 7.65 (1H, d, J=8.7 Hz), 7.79 (1H, s), 8.04 (1H, d, J=2.4 Hz). IR (Nujol); 3305, 3107, 3066, 2925, 2853, 2710, 2635, 1713, 1626, 1601, 1550 cm$^{-1}$

EXAMPLE 2–17
The following compounds were prepared in the same manner as Example 1 except for using the other acid chloride as a starting material.
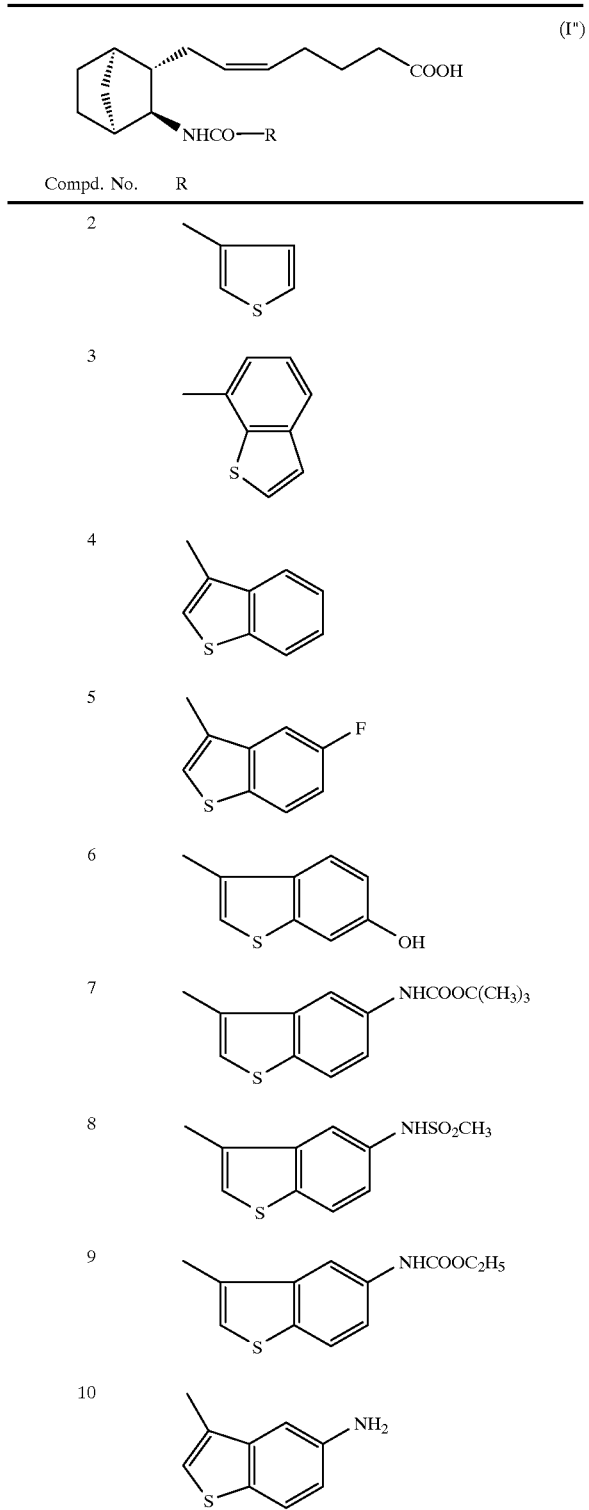
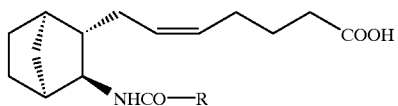
Compd. 2
$^1$H NMR δ (CDCl$_3$), 300 MHz; 1.08 (1H, m), 1.20–1.30 (2H, m), 1.45–1.50 (2H, m), 1.58–1.80 (4H, m), 2.03–2.23 (5H, m), 2.36 (2H, t, J=7.2 Hz), 2.55 (1H, s), 3.85 (1H, m), 5.31–5.45 (2H, m), 6.13 (1H, d, J=6.3 Hz), 7.33 (1H, dd, J=3.0 and 5.1 Hz), 7.39 (1H, dd, J=1.2 and 5.1Hz), 7.88 (1H, dd, J=1.2 and 3.0 Hz)
IR (CHCl$_3$); 3447, 3114, 3022, 3016, 2955, 2877, 2665, 1708, 1650, 1536, 1498 cm$^{-1}$ [α]D$^{25}$ +75.3° (c=1.02%, CH$_3$OH)
Compd. 3
$^1$H NMR δ (CDCl$_3$), 300 MHz; 1.15 (1H, m), 1.26–1.34 (2H, m), 1.45–1.56 (2H, m), 1. 61–1.77 (4H, m), 2.05–2.27 (5H, m), 2.37 (2H, t, J=7.4 Hz), 2.64 (1H, m), 3.99 (1H, m), 5.31–5.47 (2H, m), 6.45 (1H, d, J=7.5 Hz), 7.38 (1H, d, J=5.4 Hz), 7.42 (1H, t, J=7.8 Hz), 7.59 (1H, d, J=5.4 Hz), 7.63(1H, m), 7.96 (1H, dd, J=0.9 and 7.8 Hz).

IR (CHCl₃); 3453, 3117, 3063, 3031, 3017, 3012, 2955, 2876, 2669, 1708, 1650, 1585, 1567, 1519, 1495 cm⁻¹
[α]D²⁵ +62.8° (c=1.00%, CH₃OH)

Compd. 4

¹H NMR δ (CDCl₃), 300 MHz; 1.11 (1H, m), 1.22–1.34 (2H, m), 1.48–1.53 (2H, m), 1.60–1.78 (4H, m), 2.04–2.27 (5H, m), 2.36(2H, t, J=7.2 Hz), 2.62 (1H, m), 3.94 (1H, m), 5.33–5.48 (2H, m), 6.16 (1H, d, J=7.2 Hz), 7.39 (1H, m), 7.46 (1H, m), 7.86 (1H, m), 7.88 (1H, s), 8.31 (1H, d, J=7.5 1 Hz).

IR (CHCl₃); 3439, 3066, 3025, 3013, 2955, 2876, 2670, 1707, 1652, 1516, 1493 cm⁻¹ [α]D²⁵ +62.7° (c=1.01%. CH₃OH)

Compd. 5

¹H NMR δ (CDCl₃), 300 MHz; 1.08 (1H, m), 1.20–1.34 (2H, m), 1.45–1.54 (2H, m), 1.56–1.78 (4H, m), 2.03–2.24 (5H, m), 2.36 (2H, t, J=7.2 Hz), 2.61 (1H, s), 3.92 (1H, m), 5.31–5.50 (2H, m), 6.17 (1H, d, J=7.8 Hz), 7.15 (1H, dt, J=2.7 and 8.7 Hz), 7.77 (1H, dd, J=4.8 and 8.7 Hz), 7.92 (1H, s), 8.06 (1H, dd, J=2.7 and 10.2 Hz).

IR (CHCl₃); 3517, 3439, 3094, 3023, 3015, 2955, 2876, 2669, 1708, 1654, 1603, 1566, 1515 cm⁻¹
[α]D²⁴ +60.60° (c=1.00%, CH₃OH)

Compd. 6

¹H NMR δ (CDCl₃), 300 MHz; 1.08 (1H, m), 1.20–1.34 (2H, m), 1.46–1.53 (2H, m), 1.60–1.80 (4H, m), 2.00–2.37 (7H, m), 2.61 (1H, s), 3.91 (1H, m). 5.33–5.46 (2H, m), 6.16 (1H, d, J=8.1 Hz), 6.99 (1H, dd, J=2.4 and 8.7 Hz), 7.28 (1H, d, J=2.4 Hz), 7.65 (1H, s), 8.13 (1H, d, J=8.7 Hz).

IR (CHCl₃); 3598, 3510, 3437, 3101, 3029, 3017, 3006, 2955, 2876, 1709, 1646, 1603, 1559, 1518 cm⁻¹
[α]D²⁴ +61.2° (c=1.01%, CH₃OH)

Compd. 7

¹H NMR δ (CDCl₃), 300 MHz; 1.18 (1H, m), 1.30–1.33 (2H, m), 1.48–1.80 (6H, m), 1.53 (9H, s), 2.03–2.40 (7H, m), 2.07 (1H, m), 3.91 (1H, m), 5.31–5.51 (2H, m), 6.23 1H, d, J=7.8 Hz). 7.50 (1H, dd, J=1.8 and 7.8 Hz), 7.75 (1H, d, J=7.8 Hz), 8.25 (1H, m)

IR (CHCl₃): 3437, 3102, 3023, 3015, 2956, 2876, 1711, 1651, 1607, 1568, 1509 cm⁻¹
[α]D²³ +39.5° (c=1.00%, CH₃OH)

Compd. 8

¹H NMR δ (CDCl₃), 300 MHz; 1.12 (1H,m), 1.22–1.33 (2H, m), 1.42–1.54 (2H, m), 1.61–1.76 (4H, m), 2.01–2.33 (5H, m), 2.40 (2H, t, J=7.2 Hz), 2.57 (1H,m), 2.96 (3H, s), 3.91 (1H, m), 5.31–5.47 (2H, m), 6.19 (1H, d, J=7.2 Hz), 7.51 (1H, dd, J=2.4 and 9.0 Hz), 7.81 (1H, d, J=9.0 Hz), 7.88 (1H, s), 8.20 (1H, d, J=2.4 Hz)

IR (CHCl₃); 3509, 3438, 3366, 3223, 3100, 3031, 3017, 3023, 3017, 3012, 2955, 2876, 1709, 1645, 1606, 1518, 1475, 1329 cm⁻¹
[α]D²⁵ +42.3° (c=1.01%, CH₃OH)

Compd. 9

1H NMR δ (CDCl₃), 300 MHz; 1.15 (1H, m), 1.22–1.34 (2H, m), 1.33 (3H, t, J=7.2 Hz), 1.49–1.55 (2H, m), 1.61–1.82 (4H, m), 2.05–2.14 (5H, m), 2.39(2H, t, J=7.2 Hz), 2.59 (1H, m), 3.91 (1H, m), 4.25 (2H, q, J=7.2 Hz), 5.33–5.48 (2H, m), 6.21 (1H, d, J=7.2 Hz), 7.62 (1H, dd, J=1.8 and 8.7 Hz), 7.77 (1H, d, J=8.7 Hz), 7.89 (1H, s), 8.22 (1H, m)

IR (CHCl₃); 3436, 3101, 3030, 3023, 3014, 2956, 2876, 1728, 1650, 1608, 1570, 1515, 1440 cm⁻¹
[α]D²⁵ +41.8° (c=1.00%, CH₃OH)

Compd. 10

¹H NMR δ (CD₃OD), 300 MHz; 1.30–1.71 (9H, m), 2.02–2.22 (7H, m), 2.55 (1H, m), 3.82 (1H, m), 5.41–5.44 (2H, m), 6.88 (1H, dd, J=2.4 and 8.7 Hz), 7.60 (1H, d, J=8.7 Hz), 7.63 (1H, d, J=2.4 Hz), 8.02 (1H, s)

IR (Nujol); 3307, 1624, 1532 cm⁻¹
[α]D²³ +32.6° (c=1.00%, CH₃OH)

Compd. 11

¹H NMR δ (CDCl₃), 300 MHz; 1.11 (1H, m), 1.22–1.31 (2H, m), 1.45–1.54 (2H, m), 1.60–1.79 (4H, m), 2.03–2.26 (5H, m), 2.36 (2H, t, J=7.2 Hz), 2.57 (1H, m), 3.88 (1H, m), 4.00 (3H, s), 5.31–5.45 (2H, m), 6.22 (1H, d, J=7.2 Hz), 6.84 (1H, d, J=7.5 Hz), 7.34 (1H, dd, J=7.5 and 8.1 Hz), 7.44 (1H, d, J=8.1 Hz). 7.79 (1H,s)

IR (CHCl3); 3444, 3422, 3065, 3024, 3018, 3015, 2956, 2877, 2841, 2669, 1708, 1650, 1570, 1542, 1503, 1471 cm⁻¹

[α]D²¹ +91.6° (c=1.00%, CH₃OH)

Compd. 12

¹H NMR δ (CDCl₃/CD₃OD), 300 MHz; 1.16 (1H, m), 1.28–1.31 (2H, m), 1.46–1.53 (2H, m), 1.60–1.74 (4H, m), 2.04–2.22 (5H, m), 2.32 (2H, t, J=7.4 Hz), 2.57 (1H, m), 3.87 (1H, m), 5.32–5.46 (2H, m), 6.48 (1H, d, J=7.2 Hz), 6.84 (1H, d, J=7.5 Hz), 7.23 (1H, dd, J=7.5 and 8.1 Hz), 7.37 (1H, d, J=8.1 Hz), 7.79 (1H, s)

[α]D²² +44.2° (c=1.00%, CH₃OH)

Compd. 13

1H NMR δ (CDCl₃), 300 MHz; 1.14 (1H, m), 1.26–1.34 (2H, m), 1.46–1.53 (2H, m), 1.60–1.79 (4H, m), 2.03–2.25 (5H, m), 2.36 (2H, t, J=7.2 Hz), 2.41 (3H, s), 2.57 (1H, m), 3.88 (1H, m), 5.31–5.46 (2H, m), 6.25 (1H, d, J=7.2 Hz), 7.23 (1H, d, J=7.5 Hz), 7.40 (1H, dd, J=7.5 and 7.8 Hz). 7.69 (1H, d, J=7.8 Hz), 7.78 (1H, s)

IR (CHCl₃): 3443, 3422, 3030, 3010, 2955, 2877, 1756, 1708, 1650, 1564, 1540, 1504 cm⁻¹
[α]D²² +85.6° (c=1.00%, CH₃OH)

Compd. 14

1H NMR δ (CDCl₃), 300 MHz; 1.11 (1H, m), 1.23–1.32 (2H, m), 1.42–1.59 (2H, m), 1.60–1.82 (3H, m), 2.04–2.31 (6H, m), 2.37 (2H, t, J=7.2 Hz), 2.56 (1H, m), 3.93 (1H, m), 4.01 (3H, s), 5.30–5.45 (2H, m), 6.74 (1H, m), 7.13 (1H, s), 7.70 (1H, d, J=2.1 Hz), 8.26 (1H, d, J=7.2 Hz), 8.35 (1H, d, J=0.6 Hz)

IR (CHCl₃); 3397, 3026, 3015, 2955, 2877, 2654, 1709, 1642, 1623, 1538, 1475, 1459 cm⁻¹
[α]D²³ +66.7° (c=1.00%, CH₃OH)

Compd. 15

¹H NMR δ (CDCl₃), 300 MHz; 1.12 (1H, m), 1.26–1.29 (2H, m), 1.46–1.50 (2H, m), 1.57–1.78 (4H, m), 2.05–2.25 (5H, m), 2.38 (2H, t, J=7.4 Hz), 2.53 (1H, m), 3.62 (3H, s), 3.88 (1H, m), 5.32–5.45 (2H, m), 6.35 (1H, d, J=7.5 Hz), 6.80 (1H, d, J=2.1 Hz), 6.91 (1H, dd, J=2.1 and 9.0 Hz), 7.01 (1H, d, J=2.1 Hz), 7.35 (1H, d, J=9.0 Hz), 10.25 (1H, s)

IR (CHCl₃); 3446, 3242, 3022, 3012, 2955, 2877, 2834, 2654, 1707, 1626, 1586, 1541, 1507, 1480 cm⁻¹
[α]D²³ +109.1° (c=1.01%, CH₃OH)

Compd. 16

¹H NMR δ (CDCl₃/CD₃OD), 300 MHz; 1.17 (1H, m), 1.29–1.32 (2H, m), 1.45–1.74 (6H, m), 2.04–2.22 (5H, m), 2.32 (2H, t, J=7.4 Hz), 2.57 (1H, m), 3.88 (1H, m), 5.32–5.49 (2H, m), 6.38 (1H, d, J=6.6 Hz), 6.82 (1H, dd, J=2.4 and 8.7 Hz), 7.26(1H, d, J=8.7 Hz), 7.34 (1H, d, J=2.4 Hz), 7.73 (1H, s), 10.27 (1H, s)

IR (KBr); 3287, 3306, 2951, 2873, 2634, 1708, 1599, 1539, 1501, 1469, 1432 cm⁻¹
[α]D²⁶·⁵ +52.3° (c=1.01%, CH₃OH)

Compd. 17

¹H NMR δ (CDCl₃), 300 MHz, 1.14 (1H, m), 1.26–1.31 (2H, m), 1.46–1.78 (6H, m), 2.01–2.28 (5H, m), 2.33 (2H, t, J=7.2 Hz), 2.58 (1H, m), 3.84 (3H, s), 3.91 (1H, m), 5.27–5.47 (2H, m), 6.21 (1H, d, J=7.5 Hz), 6.87 (1H, dd, J=2.4 and 9.3 Hz), 7.28 (1H, d, J=2.1 and 9.0 Hz), 7.41 (1H, d, J=2.4 Hz), 7.72 (1H, d, J=2.4 Hz), 9.54 (1H, s)

IR (CHCl$_3$); 3466, 3193, 3033, 3014, 2954, 2876, 2835, 2664, 1709, 1627, 1585, 153 7, 1503, 1439 cm$^{-1}$ $[\alpha]D^{26}$ +44.3° (c=1.01%, CH$_3$OH)

EXAMPLE 18

Preparation of (5Z)-7-{(1S, 2R, 3R, 4R)-3-(5-Hydroxybenzo[b]thiophen-3-carbonylamino)-bicyclo[2.2.1]hept-2-yl}-5-heptenoic acid (18)

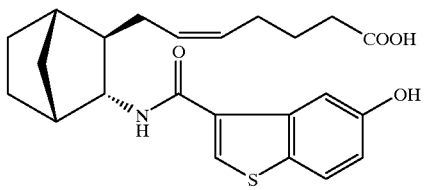

The compound 18 was prepared in the same manner as Example 1 except for using the other compound as an amino compound.

Compd. 18

$^1$H NMR δ (CDCl$_3$), 300 MHz; 1.09 (1H, m), 1.20–1.34 (2H, m), 1.45–1.54 (2H, m), 1. 57–1.70 (4H, m), 1.96–2.32 (7H, m), 2.61 (1H, s), 3.90 (1H, m), 5.26–5.46 (2H, m), 6. 19 (1H, d, J=6.9 Hz), 7.02 (1H, dd, J=2.4 and 8.7 Hz), 7.67 (1H, d, J=8.7 Hz), 7.79 (1H, s), 8.04 (1H, d, J=2.4 Hz).

IR (Nujol): 3306, 3105, 3060, 2925, 2853, 2710, 2635, 1713, 1627, 1601, 1550 cm$^{-1}$ $[\alpha]D^{25}$ −57.3° (c=1.01%, CH$_3$OH). Mp 141–142.5° C.

The compounds prepared in Examples above were tested for determining the in vivo and in vitro activities according to the method as shown in Experimental examples below.

Experiment 1
Binding to PGD$_2$ Receptor (1) Preparation of Human Platelet Membrane Fraction Blood was collected using a plastic syringe containing 3.8% sodium citrate from the vein of healthy volunteers (adult male and female), then put into a plastic test tube and mixed by slow-reversion. The sample was then centrifuged at 1800 rpm. for 10 min at room temperature, and the supernatant containing PRP (platelet-rich plasma) was collected. The PRP was re-centrifuged at 2300 rpm, for 22 min at room temperature to obtain platelets. The platelets were homogenized using a homogenizer (Ultra-Turrax) followed by centrifugation 3 times at 20,000 rpm, 10 min at 4° C. to obtain a platelet membrane fraction. After protein determination, the membrane fraction was adjusted to 2 mg/ml and preserved in a refrigerator at −80° C. until using for the binding test.

(2) Binding to PGD$_2$ Receptor.

To a binding-reaction solution (50 mM Tris/HCl, pH 7.4, 5 mM MgCl$_2$) (0.2 ml) were added the human platelet membrane fraction (0.1 mg) and 5 nM [$^3$H ]PGD$_2$ (115 Ci/mmol), and the mixture was reacted at 4° C. for 90 min. After the reaction, the mixture was filtered through a glass fiber filter paper and washed several times with cooled physiologic saline, then the radioactivity retained on the filter paper was measured. The specific-binding ratio was calculated by subtracting the non-specific binding ratio which is the radio activity similarly measured in the presence of 10 μM PGD$_2$ from the total binding. The inhibitory activity of each compound was expressed as the concentration required for 50% inhibition (IC$_{50}$), which was determined by depicting a substitution curve by plotting the binding ratio (%) in the presence of each compound, where the binding ratio in the absence of a test compound is 100%. The results are shown below.

| Compd. No | Inhibitory activity IC$_{50}$(μM) |
|---|---|
| 1 | 0.0096 |
| 2 | 0.0310 |
| 3 | 0.0870 |
| 4 | 0.0082 |
| 5 | 0.0570 |
| 6 | 0.1800 |
| 18 | 0.0055 |

Experiment 2 Evaluation of Antagonistic Activity Against PGD$_2$ Receptor Using Human Platelet Peripheral blood was collected from a healthy volunteer using a syringe in which ⅑ volume of a citric acid/dextrose solution was previously added. The sample was subjected to centrifugation at 180 g for 10 min to obtain the supernatant (PRP: platelet rich plasma). The resultant PRP was washed 3 times with a washing buffer and the number of platelet was counted with a micro cell counter. A suspension adjusted to contain the platelets at a final concentration of 5×10$^8$/ml was warmed at 37° C., then subjected to the pre-treatment with 3-isobutyl-1-methylxanthine (0.5 mM) for 5 min. To the suspension was added a test compound diluted at various concentration, and 10 minutes later, 0.1 μM PGD$_2$ was added to induce the reaction 2 minutes later, hydrochloric acid was added to terminate the reaction. The platelet was destroyed with an ultrasonic homogenizer. After centrifugation, the cAMP in the supernatant was determined by radioimmunoassay. PGD$_2$ receptor antagonism of a drug was evaluated as follows: the inhibition rate regarding cAMP increased by the addition of PGD$_2$ was determined at each concentration, and the concentration of the (drug required for 50% inhibition (IC$_{50}$) was calculated. The results are shown below.

| Compd.No. | IC$_{50}$ (μM) |
|---|---|
| 1 | 0.0039 |
| 2 | 0.3600 |
| 3 | 0.0220 |
| 4 | 0.0410 |
| 5 | 0.0340 |
| 6 | 0.0082 |
| 18 | >1.0000 |

Experiment 3
Experiment Using Nasal Blockage Model

Recently, It has been paid an attention to a theory that PGD$_2$ is one of causative substances of nasal blockage caused by allergic rhinitis, and proposed to develop an inhibitor of PGD$_2$ biosynthesis or an antagonist to the PGD$_2$ receptor as a drug reducing nasal blockage. Thus, as to the compounds of the present, invention. the anti-nasal blockage effect was evaluated by measuring the intranasal pressure of guinea pigs.

A 1% ovalbumin (OVA) solution was treated with an ultrasonic nebulizer to obtain an aerosol. Hartley male guinea pig was sensitized by inhaling the aerosol twice each or 10 min at one-week interval. Seven days after the sensitization, the guinea pig was exposed to an antigen to initiate the reaction. Briefly, the trachea of he guinea pig was incised under the anesthesia with pentobarbital (30 mg/kg. i.p.) and cannulas were inserted into the trachea at the pulmonary and nasal cavity sides. The canal inserted at the pulmonary side was connected with an artificial respirator that provides 4 ml/time of air 60 times/min. After arresting the spontaneous respiration of the guinea pig with Gallamin (2 mg/kg, i.v.), 4 ml/time of air was supplied to the snout side with an artificial respirator at the frequency of 70 times/min, and the atmospheric pressure required for the aeration was measured by using a transducer fitted at the branch. The measured pressure was used as a parameter of the nasal cavity resistance. The exposure of an antigen was carried out by generating the aerosol of 3% OVA solution for 3 min between the respirator and the nasal cavity cannula. The test drug (30 mg/kg,) was administered orally 60 min before the antigen exposure. The intranasal pressure between 0 to 30 min was measured continuously and the effect was expressed as an inhibition rate to that obtained for vehicle using the AUC for 30 min (on the vertical axis, intranasal pressure (cm $H_2O$), and on the horizontal axis, time (0–30 min)) as an indication. The result is shown below.

| Compd. No. | Inhibitory Rate (%) |
|---|---|
| 1 | 74 |

Experiment 4

Binding to $TXA_2$ Receptor (I) Preparation of Human Platelet Membrane Fraction

The human platelet fraction was prepared in accordance with Experiment 1 (1).

(2) Binding to $TXA_2$ Receptor

To a binding-reaction solution (50 mM Tris/HCl, pH 7.4. 10 mM $MgCl_2$) (0.2 ml) were added the human platelet membrane fraction (0.05 mg) and 2 nM Sodium [$^3$H](+)-(5Z)- 7-[3-endo-[(phenylsulfonyl)aminol]bicyclo[2.2.1] hept-2-exo-iy]heptenoate (Japanese Patent Publication (Kokoku) No.79060/1993, hereinafter referred to as (+)-S-145 sodium salt) (26.4 Ci/mmol), and the mixture was reacted at room temperature for 90 min. After the reaction, the resultant mixture was filtered through a glass fiber filter paper and washed several times with cooled physiological saline, then the radioactivity retained on the filter paper was measured. The specific-binding ratio was calculated by subtracting the non-specific binding ratio (the radio activity similarly determined in the presence of 10 μM (+)-S-145 sodium salt) from the total binding. The inhibitory activity of each compound was expressed as the concentration required for 50% inhibition (IC50), which was determined by depicting a substitution curve by plotting the binding ratio (%) in the presence of each compound, where the binding ratio in the absence of a test compound is 100%. The results are shown below.

| Compd. No. | Inhibitory activity to $TXA_2$ Receptor: $IC_{50}$ (μM) |
|---|---|
| 1 | 0.15 |
| 4 | 3.8 |
| 18 | 1.8 |

What is claimed is:

1. A compound of the formula (I):

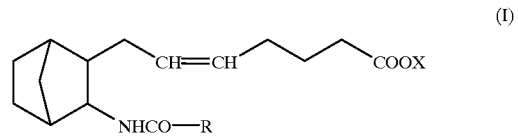

(I)

wherein R is a monocyclic or condensed heterocycle optionally substituted with an alkyl, an alkenyl, an acyl, an alkoxy, an alkylthio, an acyloxy, hydroxy, a halogen, nitro, or substituted or unsubstituted amino, provided that R is not an optionally substituted dibenzofuryl, X is hydrogen or an alkyl, and the double bond has E configuration or Z configuration, a pharmaceutically acceptable salt thereof, or a hydrate thereof.

2. The compound according to claim 1 wherein R is a monocyclic or condensed heterocycle containing only a sulfur atom(s) as hetero atom and optionally substituted with an alkyl, an alkenyl, an acyl, an alkoxy, an alkylthio, an acyloxy, hydroxy, a halogen, nitro, or substituted or unsubstituted amino, pharmaceutically acceptable salt thereof, or hydrate thereof.

3. The compound according to claim 1 wherein R is the group of the formula:

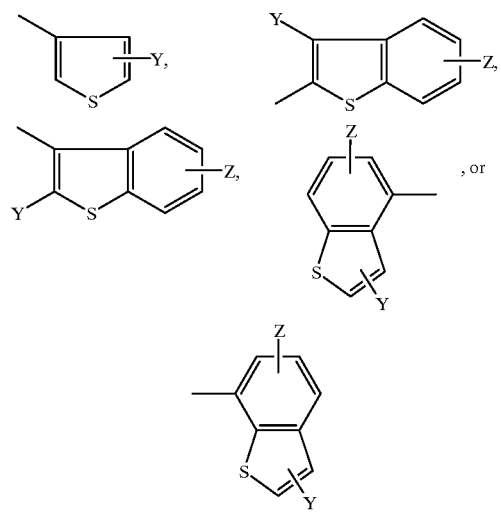

wherein Y and Z each is independently hydrogen, hydroxy, or a halogen, pharmaceutically acceptable salt thereof, or hydrate thereof.

4. The compound according to claim 1 wherein said compound is (A1) (5Z)-7-{(1R, 2S, 3S, 4S)-3-(5-Hydroxybenzo[b]thiophen-3-carbonylamino)-bicyclo[2.2.1]hepto-2-yl}-5-heptenoic acid, (A2) ((5Z)-7-{(1R, 2S, 3S, 4S)-3-(Thiophen-3-carbonylamino)-bicyclo[2.2.1]hepto-2-yl}-5heptenoic acid.

(A3) (5Z)-7-{(1R, 2S, 3S, 4S)-3-Benzo[b]thiophen-7-carbonylamino)-bicyclo[2.2.1]hepto-2-yl}-5-heptenoic acid, (A4) (5Z-7-{(1R, 2S, 3S, 4S)-3-(Benzo[b]thiophen-3-carbonylamino)-bicyclo[2.2.1]hepto-2-yl}-5-heptenoic acid, (A5) (5Z)-7-{(1R, 2S, 3S, 4S)-3-Fluorobenzo[b]thiophen-3-carbonylamino)-bicyclo[2.21]hepto-2-yl}-5-heptenoic acid, (A6) (5Z)-7-{(1R, 2S, 3S, 4S-3-(6-Hydroxybenzo[b]thiophen-2-carbonylamino)-bicyclo[2.2.1]hepto-2-yl}-5-heptenoic acid, or (A7) (5Z)-7-{(1R, 2S, 3S, 4S)-3-(7-Hydroxybenzo[b]thiophen-2-carbonylamino)-bicyclo[2.2]hepto-2-yl}-5-heptenoic acid, a pharmaceutically acceptable salt thereof, or a hydrate thereof.

5. A pharmaceutical composition comprising the compound according to any one of claims 1, 2, 3 or 4, a pharmaceutically acceptable salt thereof, or a hydrate thereof.

6. The pharmaceutical composition according to claim 5 wherein said pharmaceutical composition is antagonistic to both of $TXA_2$ and $PGD_2$.

7. The pharmaceutical composition according to claim 5 which is for treating asthma.

8. The pharmaceutical composition according to claim 5 which is for treating nasal blockage.

9. A method of treating asthma comprising administering to a subject in need thereof an effective amount of a compound according to claim 1.

10. A method of treating nasal blockage comprising administering to a subject in need thereof an effective amount of a compound according to claim 1.

* * * * *